(12) United States Patent
Zipprish

(10) Patent No.: US 7,951,285 B2
(45) Date of Patent: May 31, 2011

(54) PROCESS FOR PRODUCING A METAL BODY AND METAL BODIES

(76) Inventor: Holger Zipprish, Darmstadt (DE)

( * ) Notice: Subject to any disclaimer, the term of this patent is extended or adjusted under 35 U.S.C. 154(b) by 67 days.

(21) Appl. No.: 12/162,635

(22) PCT Filed: Jan. 27, 2007

(86) PCT No.: PCT/EP2007/000711
§ 371 (c)(1),
(2), (4) Date: Nov. 20, 2008

(87) PCT Pub. No.: WO2007/088013
PCT Pub. Date: Aug. 9, 2007

(65) Prior Publication Data
US 2009/0164027 A1    Jun. 25, 2009

(30) Foreign Application Priority Data

Jan. 31, 2006 (DE) .......................... 10 2006 004 653

(51) Int. Cl.
*C25F 3/04* (2006.01)
(52) U.S. Cl. ....................................... 205/646; 205/640
(58) Field of Classification Search .................. 205/640, 205/646
See application file for complete search history.

(56) References Cited

U.S. PATENT DOCUMENTS 5,120,405 A * 6/1992 Ito et al. .................... 205/202
6,290,834 B1  9/2001 Pearsall 2004/0033339 A1 * 2/2004 Fukutani et al. ............. 428/137
2004/0149586 A1  8/2004 Sul
2005/0060021 A1  3/2005 O'Brien et al.
2005/0103639 A1  5/2005 Lu et al.

FOREIGN PATENT DOCUMENTS

| CN | 1147625 C | 4/2004 |
|---|---|---|
| DE | 19643555 A1 | 4/1998 |
| DE | 10230720 A1 | 2/2004 |
| DE | 10234136 | 2/2004 |
| DE | 202005002450 | 7/2005 |
| EP | 0232791 A | 8/1987 |

(Continued)

OTHER PUBLICATIONS

International Search Report prepared by the European Patent Office dated Jun. 6, 2007, for International Application No. PCT/EP2007/000711; Applicant, Holger Zipprich.

(Continued)

*Primary Examiner* — Alexa D. Neckel
*Assistant Examiner* — Nicholas A. Smith
(74) *Attorney, Agent, or Firm* — Sheridan Ross P.C.

(57) ABSTRACT

The invention provides a process for producing a metal body, which leads in a simple and reliable way to formation of a defined surface topography, if desired also combined, in the range from 10 nm to 500 μm on a metal base body or blank which is to have, in particular, nanoscale pores. For this purpose, a pulsating current is applied to a metal base body in an electrolysis bath, with the electrolysis bath comprising salt former ions matched to the material of the metal base body. Furthermore, the invention provides a dental implant having particularly advantageous surface properties, in which a nanostructure is superimposed on a surface microstructure and nitrogen atoms and/or nitrogen compounds are attached and/or included in the region of the surface.

21 Claims, 12 Drawing Sheets

FOREIGN PATENT DOCUMENTS

| | | | |
|---|---|---|---|
| EP | 1159935 | A | 12/2001 |
| EP | 1449544 | A | 8/2004 |
| JP | 11 043799 | A | 2/1999 |
| RU | 2291918 | C1 | 1/2007 |
| WO | WO 2004/008984 | A | 1/2004 |
| WO | WO 2004/098436 | A | 11/2004 |
| WO | WO/2006/072804 | | 7/2006 |
| WO | WO 2006/104644 | A | 10/2006 |

OTHER PUBLICATIONS

MacDonald, D et al. "Thermal and chemical modification of titanium-aluminum-vanadium implant materials: effects on surface properties, glycoprotein adsorption, and MG63 cell attachment"; *Biomaterials, Elsevier Science Publishers BV.*, Barking, GB; vol. 25, No. 16, Jul. 2004, pp. 3135-3146.

Goransson A et al. "Bone formation after 4 weeks around blood-plasma-modified titanium implants with varying surface topographies: an in vivo study"; *Biomaterials, Elsevier Science Publishers BV.*, Barking, GB; vol. 24, No. 2, Jan. 2003, pp. 197-205.

Zhu X et al. "Effects of topography and composition of titanium surface oxides on osteoblast responses"; *Biomaterials, Elsevier Science Publishers BV.*, Barking, GB; vol. 25, No. 18, Aug. 2004, pp. 4087-4103.

Macdonald et al., "Thermal and chemical modification of titanium-aluminum-vanadium implant materials: effects on surface properties, glycoprotein adsorption, and MG63 cell attachment," Biomaterials, Elsevier Science Publishers by., Jul. 2004, vol. 25(16), pp. 3135-3146, XP 4490245.

Goransson et al., "Bone formation after 4 weeks around blood-plasma-modified titanium implants with varying surface topographies: an in vivo study," Biomaterials, Elsevier Science Publishers BV., Jan. 2003, vol. 24(2), pp. 197-205, XP 4390636.

Zhu et al., "Effects of topography and composition of titanium surface oxides on osteoblast responses," Biomaterials, Elsevier Science Publishers BV., Aug. 2004, vol. 25(18), pp. 4087-4103, XP 4497071.

\* cited by examiner

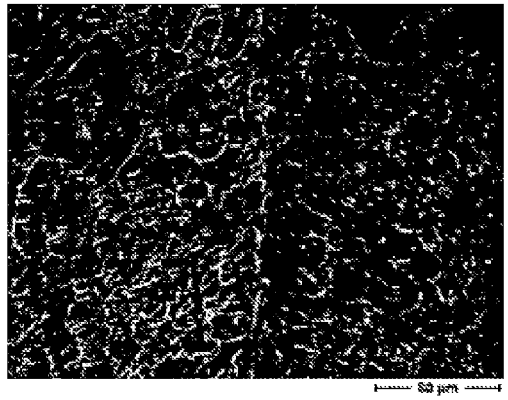
Fig. 3: Titanium surface with a structure size in the range of ca. 20 μm to 100 μm.
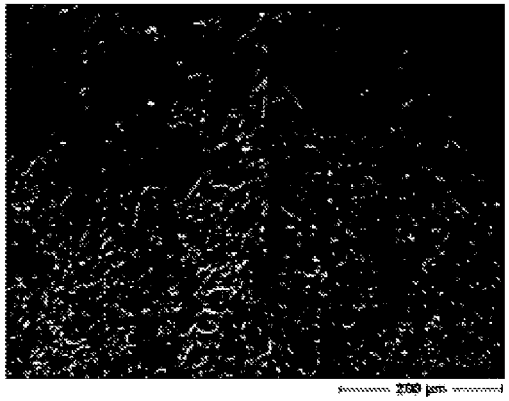
Fig. 4: Another view of Fig. 3.
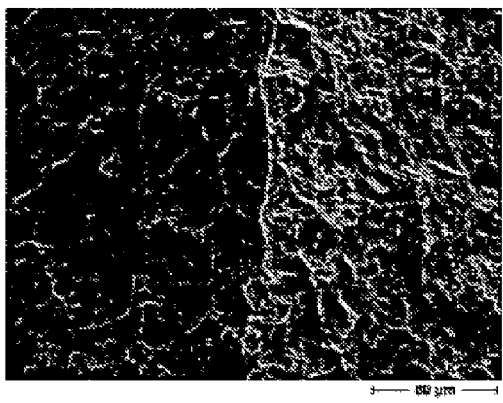
Fig. 5: Titanium surface with a structure size in the range of ca. 20 μm to 100 μm.
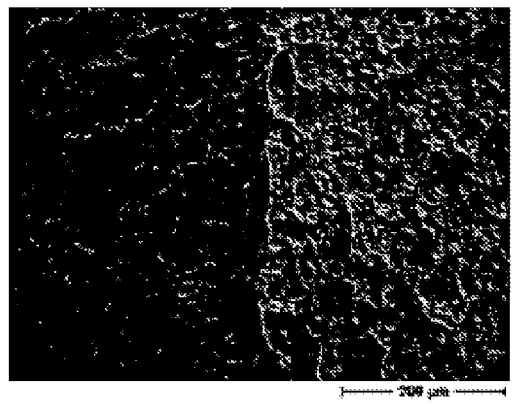
Fig. 6: Another view of Fig. 5.

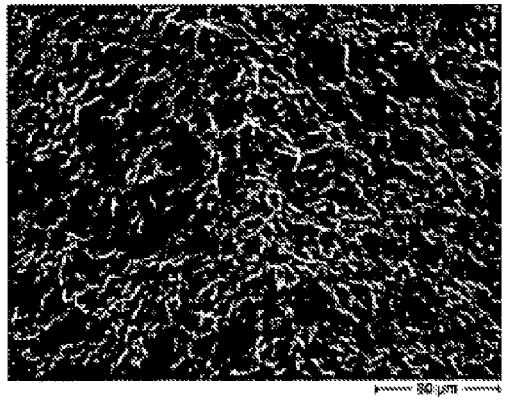
Fig. 7: Titanium surface with a structure size in the range of ca. 20 μm to 100 μm.
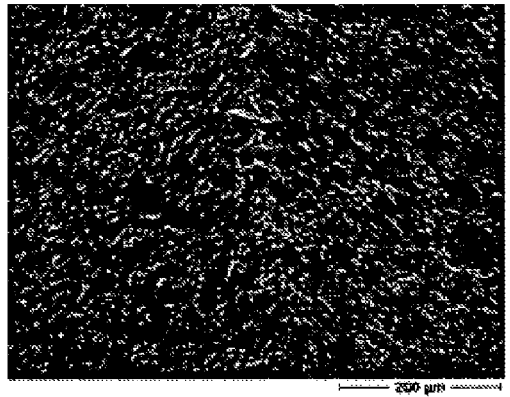
Fig. 8: Another view of Fig. 9.
Fig. 9: Microstructure smaller than 3 μm.
Fig. 10: Another view of Fig. 9.

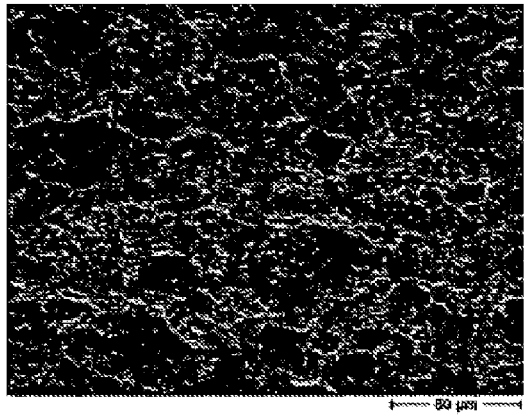
Fig. 11: Titanium implant with a sandblasted and etched microstructure.
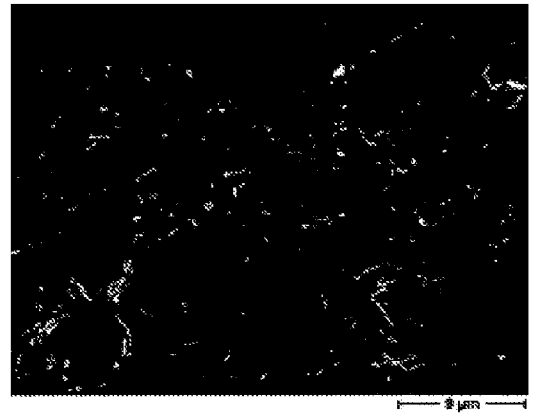
Fig. 12: Titanium implant with sandblasted inclusions.
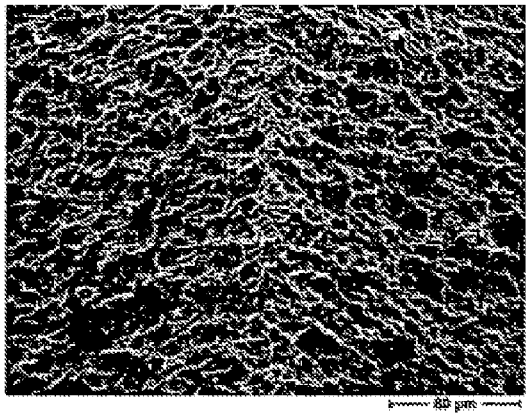
Fig. 13: Titanium surface with coarse microstructure (ca. 20 μm to 100 μm) and fine microstructure (ca. 1 μm to 10 μm).
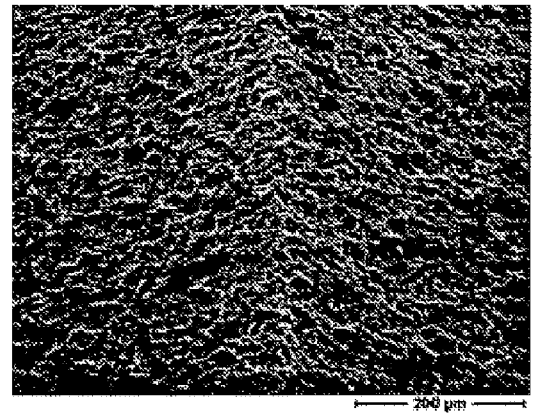
Fig. 14: Another view of Fig. 13.

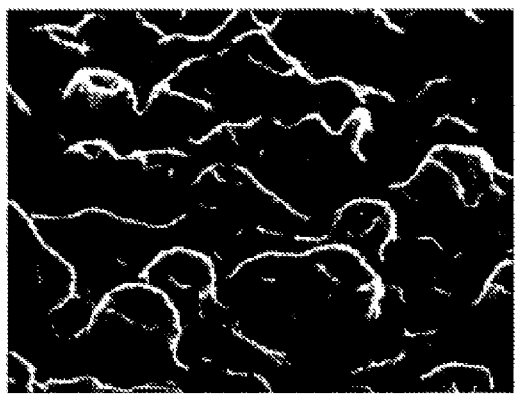
Fig. 15: Microstructure of a commercially available dental implant.
Fig. 16: Enlargement of Fig. 15.
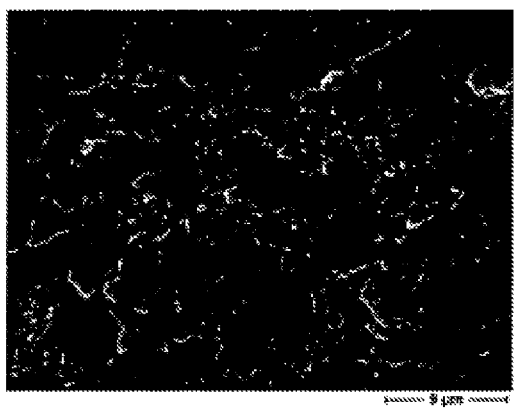
Fig. 17: Microstructure of a commercially available dental implant.
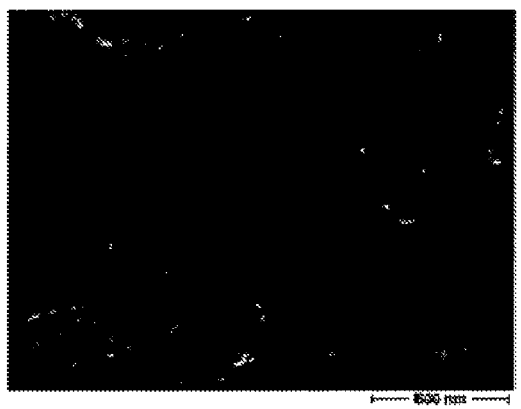
Fig. 18: Enlargement of Fig. 17.

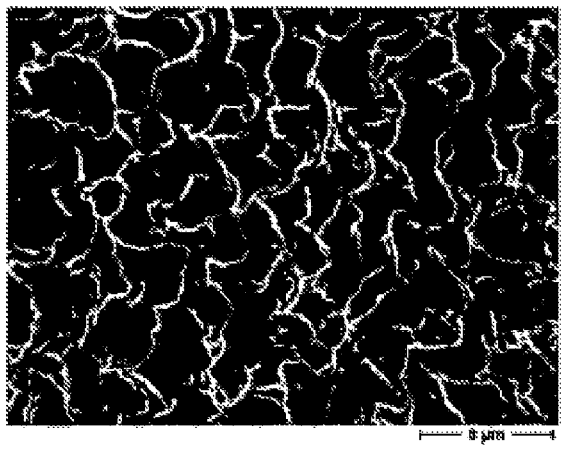
Fig. 19: Microstructure of a commercially available dental implant.
Fig. 20: Enlargement of Fig. 19.
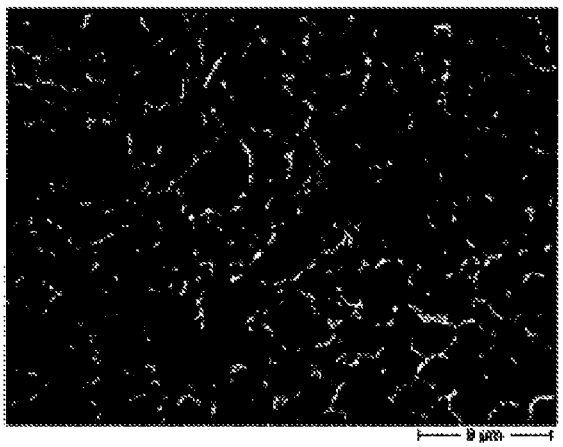
Fig. 21: Microstructure of a commercially available dental implant.
Fig. 22: Enlargement of Fig. 21.

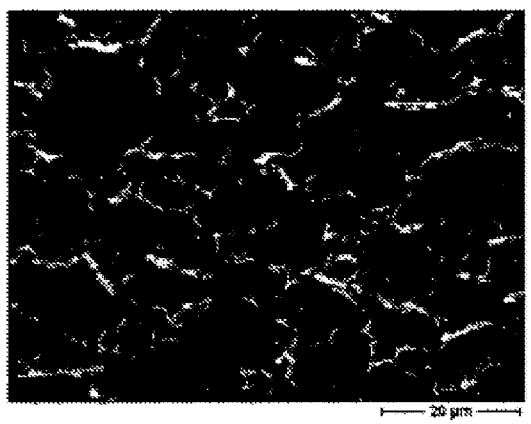 
Fig. 23: Etched microstructure.　　　　　Fig. 24: Enlargement of Fig. 22.

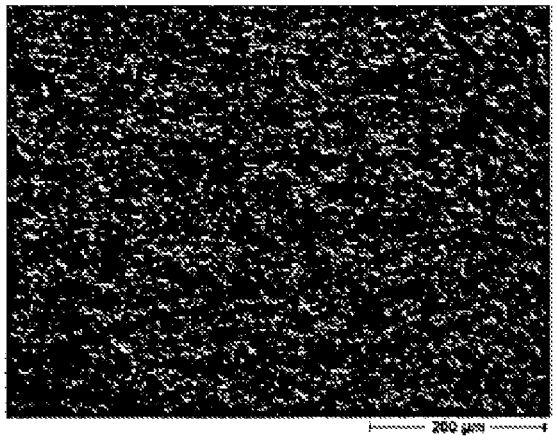
Fig. 25: Coarse microstructure (structure size ca. 20 μm – 60 μm).
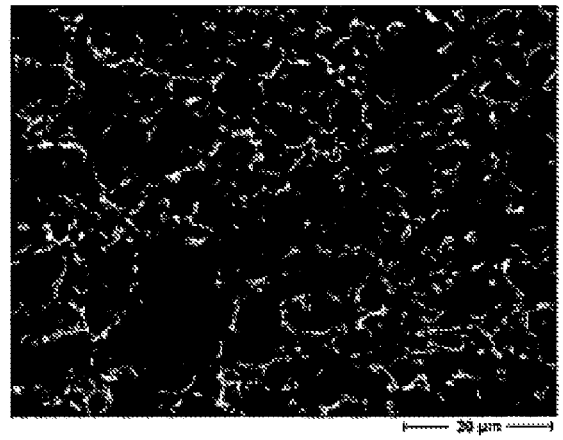
Fig. 26: Enlargement of Fig. 25. Fine microstructure (structure size ca. 1 μm – 10 μm).
Fig. 27: Enlargement of Fig. 24.
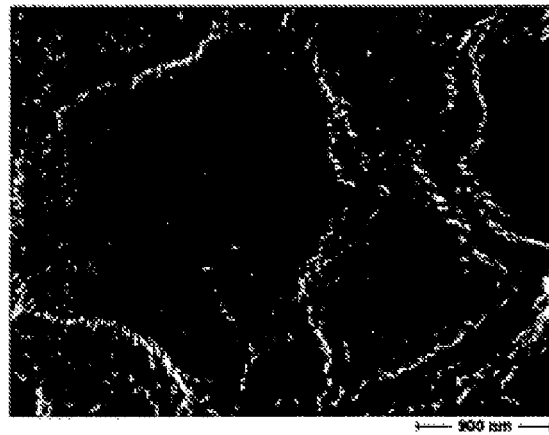
Fig. 28: Enlargement of Fig. 27. Nanostructure (structure size ca. 10 nm – 50 nm).

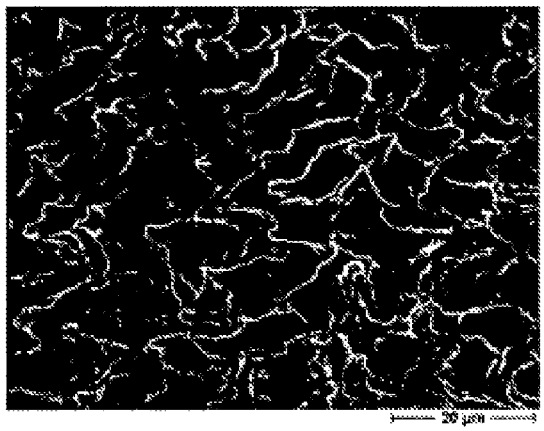
Fig. 29: Microstructured titanium surface.
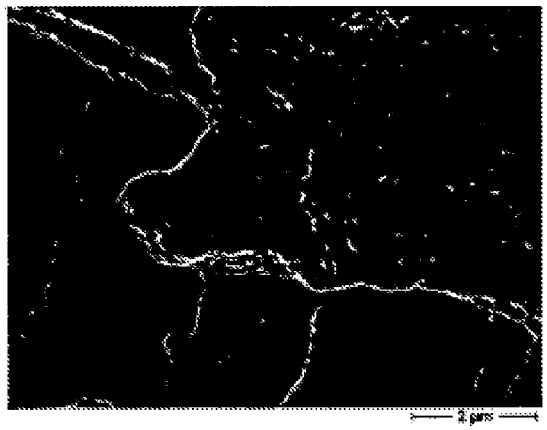
Fig. 30: Enlargement of Fig. 29. A superimposed nanostructure can be seen.
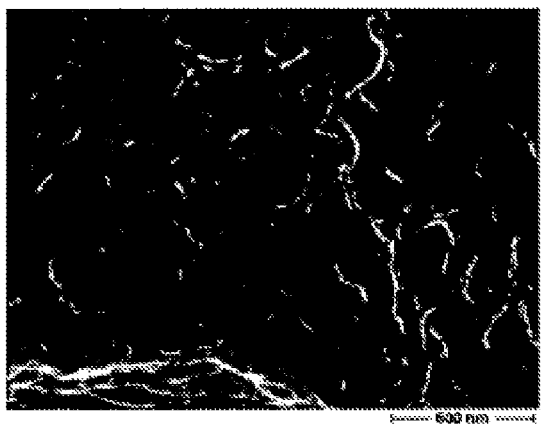
Fig. 31: Enlargement of Fig. 30.
Nanopores in the range of ca. 10 nm – 150 nm.

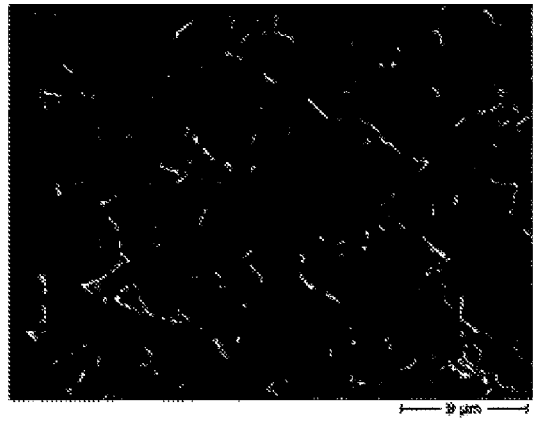
Fig. 32: Microstructured titanium surface.
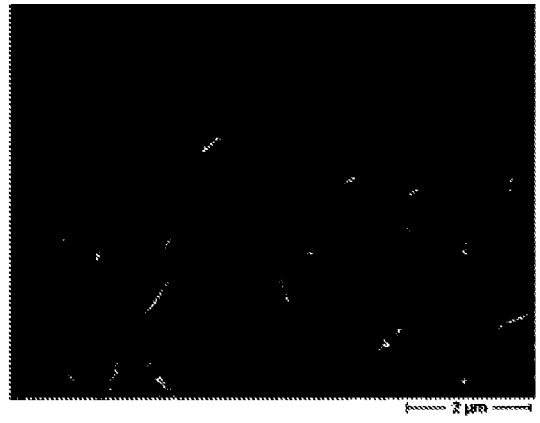
Fig. 33: Enlargement of Fig. 32. A superimposed nanostructure can be seen.
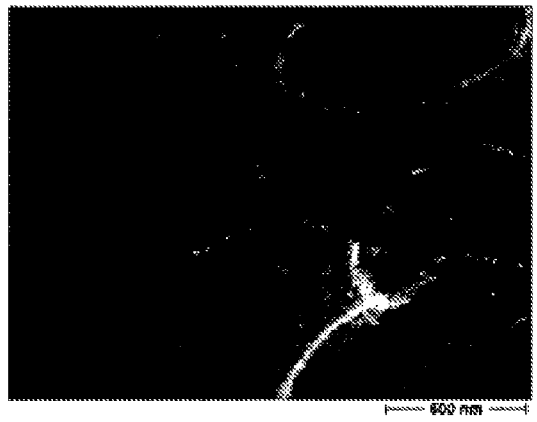
Fig. 34: Enlargement of Fig. 33.
Nanostructures (elevations) in the range of ca.
10 nm – 150 nm.

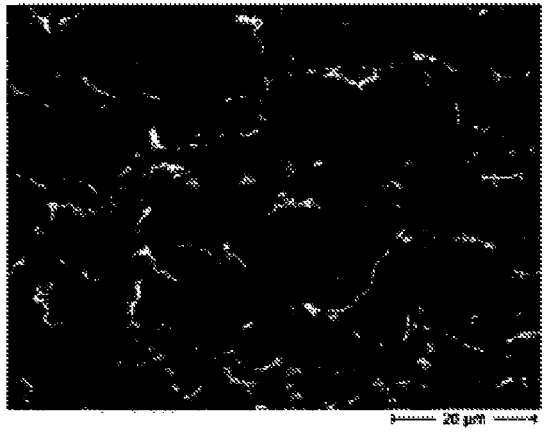
Fig. 35: Microstructured titanium surface.
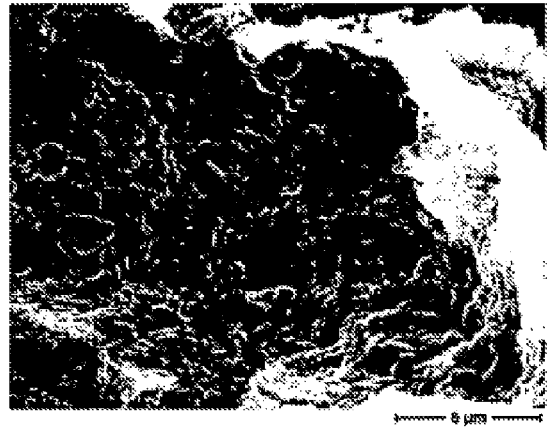
Fig. 36: Enlargement of Fig. 35. A superimposed nanostructure can be seen.
Fig. 37: Enlargement of Fig. 36.
Nanostructures (elevations) in the range of ca.
10 nm  150 nm.

PROCESS FOR PRODUCING A METAL BODY AND METAL BODIES

CROSS REFERENCE TO RELATED APPLICATIONS

This application is a national stage application under 35 U.S.C. 371 of PCT Application No. PCT/EP2007/000711 having an international filing date of 27 Jan. 2007, which designated the United States, which PCT application claimed the benefit of German Application No. 10 2006 004 653.6 filed Jan. 31, 2006, the entire disclosure of each of which are hereby incorporated herein by reference.

The invention relates to the manufacture of a metal body, particularly for use as a bone implant, particularly as a dental implant. It further relates to a metal body and a bone implant which can be obtained according to the process.

Dental implants are known in a variety of forms. They are usually inserted into the jawbone by screwing in at the site of an extracted or lost tooth in order to hold, after a healing period of three to four months, a prosthetic assembly part or a crown serving as a tooth replacement. For this purpose, such a dental implant is usually designed as a suitably shaped metal body and shaped in the manner of a pin and has at its apical end a usually self-cutting screw thread with which the pin is inserted into the appropriately prepared implant bed.

Generally, dental implants are made from titanium, zirconium, niobium or tantalum or from histocompatible alloys which contain one of these elements as the primary component. In all of these implants, the goal is that the osseous tissue be given the opportunity to bind quickly and permanently with the implant surface. This process is also referred to as osseointegration. In this context, it has already been known for quite some time that the microscopic structure is of particular importance. In particular, up to now, porous surfaces with a pore size in the micrometer range have proven advantageous. Through the increased contact surface between implant and bone, the bone growth is promoted and hence the bone attachment rate after the postoperative trauma is increased.

In addition, implants with a so-called "pore-in-pore" structure are known from EP 1 159 935 A1 in which relatively coarsely-pored surface structures are first produced through radiation processing into which fine pores are then etched, so that roughness is superimposed onto different length scales. Moreover, dental implants with a homogeneous nanostructured surface are known from DE 20 2005 002 450 U1. Such nanostructured surfaces appear to promote the growing in of the implants and the integration into the osseous tissue as a result of a particularly favorable wetting behavior.

Processes for the surface structuring of metal bodies known up to now, particularly for use as dental implants, include sandblasting, etching, electrolytic etching, laser treatment, spark erosion, plasma spraying or even high-temperature electrolysis. They are either associated with great tedium and expense or leave behind undesired impurities on the surface. Moreover, with the exception of laser technology, it is not possible according to the current state of knowledge to transfer the entire topographical area from 10 nm to 500 µm onto a surface. This means that, in order to superimpose pores in pores (see EP 1 159 935 A1) or a fine structure (e.g. nanostructure, i.e. structure size of less than 100 nm) on a coarser structure (structure size ca. 1 µm to 5 µm), it is necessary to use various processes. In the present invention, one is given the possibility of first producing a coarse microstructure (structure size greater than 20 µm), superimposing a finer microstructure (structure size ca. 0.5 µm to 20 µm) on same and superimposing a nanostructure (structure size 10 nm to 500 nm or 10 nm to 250 nm, preferably 10 nm to 100 nm) on both structures. Nanostructures in particular which have defined geometric parameters or surface topographies on a nanometer scale with specific (bio)physical or chemical characteristics that offer heightened clinical benefit in comparison to conventional microstructured implant surfaces in oral implantology at reasonable manufacturing cost have been possible to produce only with difficulty, if at all, using the methods known up to now. In addition, the known processes for surface structuring are often susceptible to faults with respect to unavoidable interferences and parameter fluctuations during process control and hence oftentimes lead to artifacts and production rejects.

It is therefore the object of the invention to provide a process for producing a metal body with which surface enlargement can be obtained in a particularly favorable and reliable manner, wherein the surface texture with respect to the microscopic roughness and/or nanoscopic pores/structures which ensure especially favorable microretention characteristics and/or especially favorable wetting characteristics can be achieved by means of the process parameters (etching medium/electrolyte, applied potential waveform, current density, temperature, duration of application, etc.). Moreover, a metal body with the aforementioned especially advantageous surface characteristics is to be proposed which is especially suited particularly for growing into the bone for use as a dental implant and/or as an orthopedic implant (e.g. hip joint implant).

With regard to the process, the object is achieved according to the invention by applying a pulsing current to a metal base body in an electrolysis bath, with the electrolysis bath being laced with ions each of which respectively consist of an element from one of the main groups V to VII of the periodic table or comprise such an element as a component.

Completely surprisingly and unexpectedly, it turns out that this very process leads to the formation of surface structures which ensure especially favorable wetting characteristics and stimulate osseointegration, which is to say the attachment of the bone to the implant surface, especially well when the metal body is used as a dental implant. Namely, through the treatment of the metal base body in the manner of an electrolytic etching with a pulsing electrolysis current, a specific nanostructure is formed on the surface. A plurality of relatively small pores or recesses with an average extension in the sub-micrometer range, preferably smaller than 200 nm, can be found here. Such structures can be detected, for example, using electron microscopic imaging.

It is assumed that the application of a pulsing current, i.e. a current which changes relatively drastically in a relatively short period of time, to the metal base body breaks through the oxidic surface layer—actually always present in a metal body—locally and in a statistically distributed manner, so that the etching compound temporarily comes into direct contact with the actual metal. By means of the reaction partners prepared in the electrolysis bath, which are selected such that they form suitable chemical compounds with the respective metal material, the etched-out metal ions are bonded and subsequently precipitated, for example, or dissolved in the electrolyte and thus permanently removed from the metal base body. It is supposed that the broken-open oxidic surface layer of the metal base body is then regenerated, so that the etching process comes again to a standstill, thus leaving behind local craters with nanoscopic dimensions. This process appears to begin again with the next current pulse, with the oxidic surface layer being destroyed again locally and temporarily and in a statistically distributed manner at other locations on the metal base body.

The reaction partners provided for the metal of the base body, i.e. the ions with components from main groups V to VII of the period table, can act here, in particular, as salt-formers for the respective metal. Particularly, the electrolysis bath can comprise ions which consist of the elements nitrogen (N), oxygen (O), fluorine (F), chlorine (Cl), sulfur (S) and/or phosphorus (P) or comprise them as components.

Precisely these nanostructures occurring in this process appear, in general, to promote the wetting behavior of the metal body or, when used as a dental implant, to also promote collagen and cell bonding. In particular, the chemical characteristics of the surface in the micrometer range and in the nanometer range play a crucial role here as well (e.g. hydrophilic or hydrophobic, doped or pure, etc.). In the present case, an advantage of the metal or implant surfaces manufactured or prepared using the processing according to the invention which is especially important for oral implantology appears to consist in that it has a decidedly hydrophilic nature which is not lost even after long-term contact of the metal body with the atmosphere, for example. The contact angle which a drop of liquid wetting the surface forms with the surface is particularly indicative of the hydrophilic nature. As has been shown, metal surfaces treated according to the new process lead, particularly in the case of water, to an extremely good wettability with contact angles of less than 10°. This means that drops of liquid on the surface have the shape of a very flat spherical cap. What is more, the hydrophilic nature of the manufactured metal bodies expressed by this remains lastingly intact even over a period of more than several days.

The metal base body expediently consists of titanium or of a titanium-containing alloy, particularly laced with chromium. Besides its great strength, titanium is also very resistant to corrosion and is highly biocompatible. However, in principle, other metals or noble metals are also worthy of consideration as implant materials or as components thereof, e.g. zirconium, niobium or vanadium. Advantageously, ions with elements from main group V, VI and/or VII of the periodic table, particularly a sulfate ion ($SO_4^{2-}$) and/or nitrate ion ($NO_3^-$) and/or nitrite ions ($NO_2^-$) and/or fluorine ions ($F^-$) and/or chloride ions ($Cl^-$) and/or ions of sulfuric acid ($SO_3^{2-}$) and/or sulfide ions ($S^-$) and/or phosphate ions ($PO_4^{3-}$) are [used] as electrolyte for the preparation of the salt-forming ions, with these materials being especially suitable for the bonding of etched-out titanium ions particularly in a metal body made of titanium. Other suitable salt-forming ions can be, for example, chloride ions ($Cl^-$) or phosphate ions ($PO_4^{3-}$).

Advantageously, one of the acids from among sulfuric acid ($H_2SO_4$), nitric acid ($HNO_3$), hydrochloric acid (HCl), nitrous acid ($HNO_2$), phosphoric acid ($H_3PO_4$), sulfurous acid ($H_2SO_3$), fluoric acid (HF), a mixture of at least two of the abovementioned acids, or an aqueous solution with salt of the abovementioned acids or mixture thereof is used as electrolyte. In an alternative variant, however, an aqueous sodium sulfate solution or an ammonium sulfate solution or a sodium nitrite solution or an ammonium nitrite solution can also be provided as electrolyte. In this case, a concentration of approximately 5 g sodium sulfate ($Na_2SO_4$) or ammonium sulfate (($NH_4)_2SO_4$) or sodium nitrite ($NaNO_2$) or ammonium nitrite ($NH_4NO_2$) per 30 ml water ($H_2O$) is preferably employed. Other electrolyte solutions can also be used, however, in which, for example, sulfates, sulfides, nitrates, nitrides, chlorides, fluorides or phosphates are dissolved in an aqueous or non-aqueous liquid. The electrolyte temperature during the execution of the process should be selected above about 0° C. and below the boiling temperature of the electrolyte and is advantageously 400° C. to 120° C., particularly about 50° C.

Another possibility is to melt salts or a mixture of several salts and to use them as etching medium/electrolyte. There are possibilities here of a melt of hxdrate[sic]-bonded salts (e.g. calcium) which dissolve in their own water of crystallization or melted, water-free salts. One variant is melts of calcium chloride hexahydrate at temperatures greater than 30.2° C. Another example is the application of an alternating current with or without direct current component to a high-temperature electrolysis.

Advantageously, the temporally pulsing or changing electrolysis current is an alternating current, which therefore changing direction periodically. Here, a direct current component is preferably superimposed on the alternating current such that the metal base body is exclusively active as an anode and not as a cathode. A square-wave alternating current, preferably with corresponding direct current component, is especially advantageous in view of the desired surface structures and their microbiological, chemical and physical characteristics.

Moreover, it is advantageous if an alternating current with a frequency of preferably 1 Hz, particularly greater than 1 Hz, is applied to the electrodes of the electrolysis bath, with the amplitude [of the current] being increased in successive time intervals on a stepped basis, preferably in steps of approximately 5 V or less, from approximately 5 V to 30 V. Here, the reduction of the voltage caused by the alternating current, a comparatively slow increase of the voltage with respect to the increment and a longer dwell time at the respective voltage level prevent an uncontrolled removal of material from the implant surface. It turns out that an interval length of ca. 5 minutes represents an especially favorable compromise with regard to a reliable and targeted process control on the one hand and a total duration of the treatment that is reasonable from an economic perspective and not too lengthy on the other hand.

On the other hand, however, it also turns out that especially favorable treatment results can be achieved by advantageously selecting a particularly high voltage change rate of at least 1 V/s, preferably greater than 10 V/s, particularly greater than 1000 V/s, in the phases of the voltage change, i.e. in the so-called transient phases. The best results have been achieved with the voltage change rates of a square-wave signal. In this way, relatively intense, pulse-like voltage changes can be achieved in the positive and negative direction which apparently promote the desired nanoscopic formation of surface structures especially well.

In an especially advantageous embodiment, a bone implant for medicinal purposes, particularly for insertion into the human body, preferably a dental implant or hip implant, is manufactured using the process. To this end, an implant base body provided with a microstructured, preferably electrically or electrochemically produced surface is preferably used as a metal base body. The implant surface of the thusly manufactured dental implant has, on the one hand, a plurality of irregularly arranged but statistically speaking approximately homogeneously distributed micropores or "craters" with an average extension of ca. 0.5 µm to 100 µm, preferably 0.5 µm to 20 µm, with the nanopores produced by the pulsed etching being respectively arranged within these micropores on the other hand. Dental implants designed in this manner emphatically support and speed up the bone-forming cells, the osteoblasts, [and] the healing process taking place after implantation. Just the same, the manufacturing process for the implant can be executed and controlled relatively simply and costeffectively even on an industrial scale. The process parameters are preferably selected here such that a nanostructure, superimposed on the microstructure, of the type described in the foregoing is formed on the surface of the implant base body.

At the beginning of the electrolytic etching aimed at producing the nanostructure, the implant base body should preferably already be provided with a microscopic surface structure and/or be chemically activated. This pretreatment plays an important role with regard to the achievable final results. Two of the following six pretreatment methods have proven to be especially effective:

Pretreatment Methods:
1. In a first advantageous variant, the inventive process itself is used for the primary structuring of the surface. The microstructure is produced on the surface of the implant base body in a process step preceding the nanostructuring in that the implant base body is first subjected to a pulsing current in an electrolysis bath, with an aqueous solution containing chloride ions (Cl⁻) or containing hydrochloric acid as the main component used as electrolyte, and with the implant base body being dipped subsequently into an acid bath, preferably a sulfuric acid bath. In so doing, a layer consisting of the electrolytic reaction products first forms on the implant base body, [with the layer consisting] particularly of titanium/chlorine compounds. This is subsequently removed by dipping the implant into an acid bath, preferably a sulfuric acid bath.
2. In an alternative variant, the microstructure is etched in a preceding process, preferably by electrolysis. The acids hydrochloric acid, phosphoric acid, fluoric acid, sulfuric acid or nitric acid or a mixture of at least two of the acids can be used as basic etching medium/electrolyte.
3. Another pretreatment method is etching or electrolytic etching in melted salts which have dissolved in their own water or crystallization, preferably melted, water-free salts. In particular, this can be performed as high-temperature electrolysis (HTE).
4. Another pretreatment method is the chemical, electrolytic coating, particularly executed as a high-temperature electrolysis method, with titanium, zirconium, tantalum, niobium, chromium, iron or an alloy with one of the above-mentioned elements as the main component.
5. Sandblasting, spark erosion, laser treatment, plasma spraying or other abrasive surface processes can also be mentioned as further pretreatment processes.
6. Moreover, the combination of one or more of the above-mentioned pretreatment methods leads to a variation of the surface topography.

With regard to the metal body, the aforementioned object is achieved in that its surface has a hydrophilic wetting angle of no more than 15°, and/or in that the nanoscopic pores have an average pore diameter of no more than 250 nm or the nanoscopic structure has a structure size of no more than 250 nm. In a particularly advantageous manner, the aforementioned process for producing such a metal body is used. As it turns out, namely, a structure primarily characterized by pores in the surface or, alternatively, primarily by elevations on the surface can occur as the result of the electrolytically pulsed etching.

The lateral dimensioning should lie here in the nanoscopic range in any case, so that the desired surface characteristics with respect to hydrophilia or with respect to bone growth can be achieved as well. In the case of the formation of surface elevations, they should consequently have lateral extensions of no more than about 250 nm on average.

Here, the metal body is preferably embodied as a bone implant, especially preferably as a dental implant, preferably made of titanium or of a titanium-containing alloy, advantageously with a microstructured surface, with a nanostructure being superimposed on the microstructure, and with nitrogen atoms and/or nitrogen compounds being preferably attached or included in the area of the surface. This is based on the idea that, through the targeted insertion or application of nitrogen atoms into the atomic or molecular compound of the implant surface in the manner of nitrogen doping, a particularly positive influence can be exercised on the bone attachment.

The advantages achieved with the invention consist particularly in that, by means of a simple and cost-effective electrochemical process, a metal body, particularly for use as a dental implant, can be produced with a nanostructure and a nanoroughness which has an advantageous effect on the healing process after the anchoring of the implant in the jawbone and particularly on the strength that can be achieved in the connection between bone and implant. Through the doping of foreign atoms, particularly nitrogen atoms, into the implant surface, the effect can be amplified even more. Moreover, due to the nano-scale surface structure of the metal body and the hydrophilic characteristics and/or capillary effects associated therewith, liquids can be introduced with particular ease and effectiveness into the surface. This could be used, for example, to place medications or other agents or reagents on the surface. Due to the good wettability, however, other advantageous applications are also conceivable, with the application of paints, adhesives or other surface coatings onto the metal body being facilitated considerably.

The especially favorable hydrophilic behavior of the treated surface obtained through the nanostructure or nanoroughness can be seen, for example, in the characteristic wetting angle obtained therein, which is particularly less than 15%. In addition, the thusly obtained hydrophilic behavior remains longer through the nanopores, nanostructures, doping or attachment of nitrogen atoms/compounds and/or lasts on the surface longer than in a metal surface that has been chemically or electrochemically activated.

Sample embodiments of the invention are explained in further detail on the basis of a drawing.

FIG. 3 to FIG. 37 show a number of electron microscope images of the implant surfaces produced through the electrolytic treatment.

Figure 1:
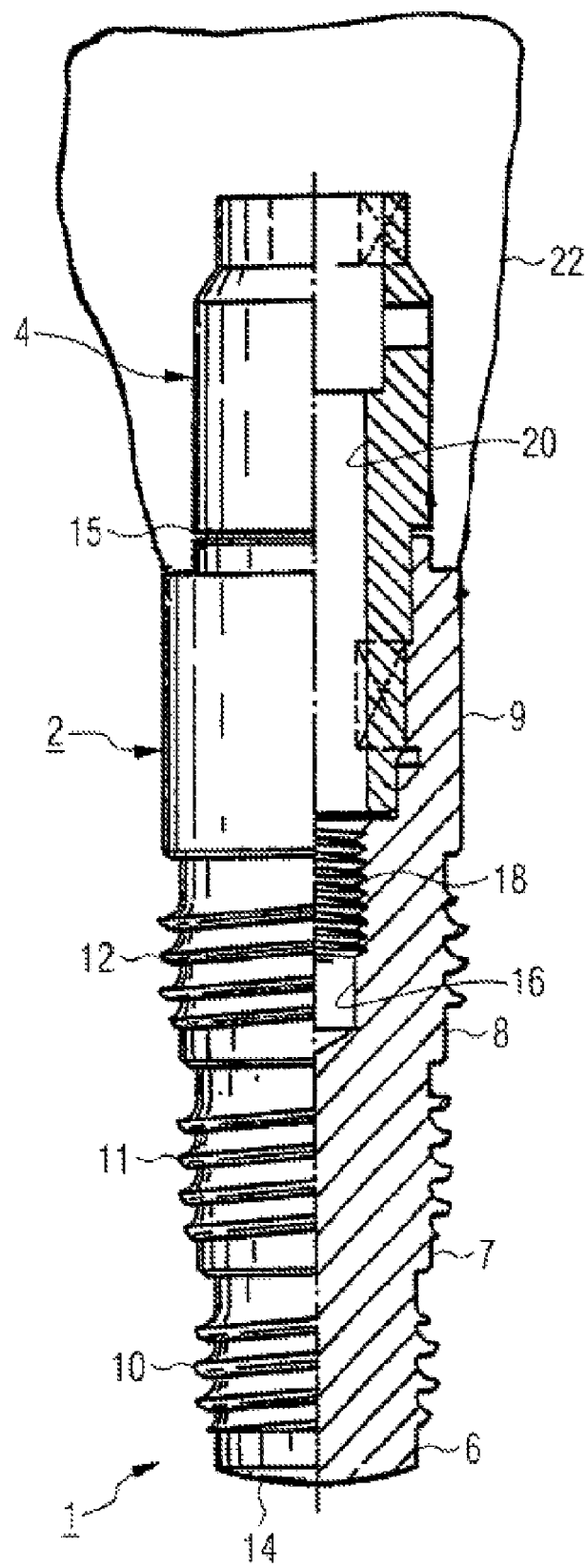
FIG. 1 shows a dental implant viewed in a partial lateral section.

FIG. 1 shows, partially in one view and partially in axial section, a two-part dental implant 1 with a post part 2 and an assembly part 4. The post part 2 as well as the head or assembly part 4 consist of metal, particularly of titanium or a titanium alloy. The post part 2 is embodied as a step screw and contains three steps 6 to 8, each of which has a self-cutting thread 10 to 12 with the same increment. The step 6 nearest the apical end 14 has the smallest diameter. By contrast, the step 9 nearest the assembly part 4 has a smooth, cylindrical outer surface. The post part 2 has on its coronal end 15 an internal borehole 16 into which the head or assembly part 4 is inserted and which further contains an internal thread 18. The connection of the assembly part 4 to the post part 2 is done with a screw (not shown here) which is guided through a through hole 20 of the assembly part 4 and screwed into the internal thread 18. A crown 22 or the like can be joined in a known manner with the assembly part 4.

The post part 2 is anchored in an appropriately prepared implant bed of the jawbone. Here, the threaded construction ensures a high level of primary stability and an equal transfer into the jawbone of the forces occurring during chewing. Moreover, the bone should grow as directly as possible against the implant during the healing phase following the implantation and join closely together with same. This process, referred to as osseointegration, is improved considerably through a roughening of the implant surface. Many implants offered on the market differ in terms of the process of roughening and surface structuring, and no particular type of surface processing has become generally established from a scientific or commercial standpoint. By contrast, there exists the need for the development of new processes which lead to improved characteristics and, in so doing, particularly take into account, implement and further develop the insights of nanostructure research.

Figure 2:
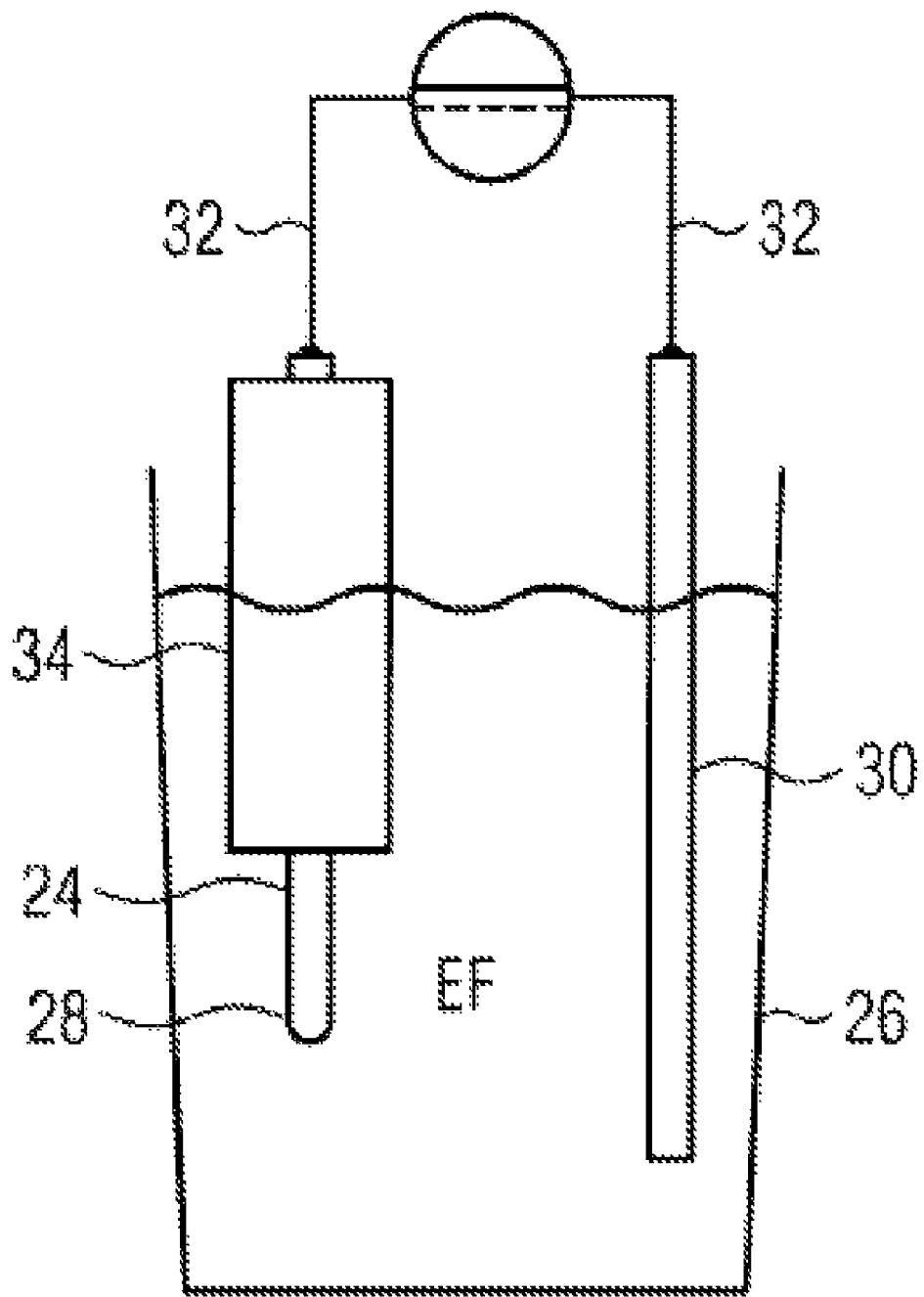
FIG. 2 shows a schematic view of a device for the electrolytic treatment of a dental implant.

In the present case, electrolytic etching processes are substantially used which build on a pretreatment of an implant blank for nanostructuring, so that a microstructured surface with included nanopores forms overall. The two process steps are each executed in an electrolysis device as represented schematically in FIG. 2. The implant base body or titanium blank 24 to be treated dips here at least partially into an electrolyte liquid EF stored in a container 26 and forms an electrode 28. Spaced from this first electrode 28, a second electrode 30 made of titanium, platinum or gold dips into the electrolyte liquid EF. The two electrodes 28, 30 are connected via electrically conductive wire connections 32 to a controllable current source which delivers an electrical current that is constant in time or varies in time, as needed. In the sample embodiment, the implant base body 24 is held mechanically by an electrically insulating holding element 34, with an electrically conductive internal element (not visible in FIG. 2) being fed through the holding element 34 for electrical contact. As a result of the ions dissolved in the electrolyte liquid EF and traveling from electrode to electrode, the electric circuit is closed. The metal ions or electrodes are reduced here at the cathode to pure metal through the addition of electrons. The anode material is oxidized into metal ions under the emission of electrons. The temperature of the electrolyte liquid EF can be adjusted by means of a controllable heating unit (not shown here).

I. Microstructuring of the Implant Surface

An aqueous solution of 30 ml water ($H_2O$) and 5 g sodium chloride (NaCl) or of 30 ml water ($H_2O$) and 5 g ammonium chloride ($NH_4Cl$) is selected as electrolyte. Alternatively, other salts which release chloride ion ($Cl^-$) upon dissolution in water, or hydrochloric acid (HCl) can also be used. The electrolysis is performed at an electrolyte temperature of 50° C. to 60° C., with the titanium implant being active as an anode (so-called anodic power supply). Lying between the anode and the cathode is a square-wave voltage signal pulsing between 0 V or less and a maximum value at a frequency of 1 hertz. The maximum value, i.e. the amplitude of the square-wave signal, is increased in successive time intervals of 5 minutes, respectively, in 5 V steps from 5 V to 30 V. Through the pulsing of the voltage and the slow increasing of the amplitude, an uncontrolled reaction is avoided that would otherwise bring about an uncontrolled removal of material in some areas of the implant while producing no reaction in other areas.

The titanium/chlorine compounds produced during electrolysis as reaction products are not soluble in the electrolyte. The reaction products grow on the surface of the dental implant outward, on the one hand, and attack same on the other hand under the formation of recesses (etching effect). This process occurs on the surface relatively unevenly.

Subsequently, the reaction products are removed by dipping the implant into a temperature-controlled (e.g. 60° C.) sulfuric acid bath. In this case, a dwell time of about 30 to 60 minutes in the sulfuric acid bath is expedient and sufficient. After the thusly achieved removal of the layer composed of reaction products, the surface of the dental implant has a roughness with a structure size in the range of 20 μm to 100 μm on which structures with a size of less than 1 μm or greater than 100 μm can be sporadically superimposed. Through the variation of the time interval and the rate of increase (in volts per step) during the electrolysis preceding the sulfuric acid bath, the roughness can be varied.

II. Nanostructuring of the Implant Surface a) Variant 1

The implant base body pretreated according to the process described above and hence already microstructured is dipped into an aqueous electrolyte solution in which 5 g sodium sulfate ($NaSO_4$) or 5 g ammonium sulfate ($(NH_4)_2SO_4$) is dissolved in 30 ml water, and then a square-wave alternating current with a frequency of 1 Hz is applied to it at an electrolyte temperature of 50° C. The sulfate ions ($SO_4^{2-}$) thusly retained in the electrolysis bath serve as salt-formers and hence as suitable reaction partners for the metallic titanium. Alternatively, a 98% sulfuric acid or a 60% phosphoric acid can also be used as electrolyte, for example. A square-wave alternating current with an initial amplitude of 5 V is present at the electrodes 28, 30 of the electrolysis device, which is to say on the dental implant 24 and at the second electrode corresponding thereto, with this current being slowly increased in 5 V steps up to at least 10 V, preferably 60 V or greater than 60 V. The dwell time in the respective time interval is 5 minutes, thus resulting in a total duration of treatment of about a half-hour.

During treatment, a titanium oxide layer forms on the implant which evenly covers the microstructures already present from the onset. In addition, a nanostructure is formed which is impressed or superimposed on the microstructure and whose pores have an average expansion of less than one micrometer, usually 10 nm to 900 nm, depending on the set process parameters. Several examples of the thusly produced surface structures are shown in the electron microscope images in FIG. 3 to FIG. 37, each with different magnification factors. The scale is indicated within each of the figures. The surfaces are strongly hydrophilic, which leads to an especially intimate wetting upon contact with liquids.

b) Variant 2

Variant 2 can be applied both with and without one of the six aforementioned pretreatment methods. A solution of 5 g sodium nitrite ($NaNO_2$) in 30 ml water or 5 g ammonium nitrite in 30 ml water is provided as electrolyte. Alternatively, a 60% nitric acid can also be used. Otherwise, the details of the process control and the parameters match those named under II a). Here, a superimposition of three structures (see FIGS. 23 to 26) can occur. That is, a fine microstructure with a roughness of ca. 1 μm to 10 μm is superimposed on a coarse roughness of ca. 20 μm to 60 μm, and a nanostructure with a structure size of ca. 10 nm to 50 nm is superimposed on this. Moreover, elementary nitrogen or nitrogen compounds can attach or embed on the surface.

FIGS. 3 to 8 show three possibilities of the first pretreatment method. This process step can replace the preceding sandblasting step in other etching methods (for a comparison with a surface on the market, see FIG. 11) with equal or similar surface topography and, in this manner, prevent undesired inclusions of the blasting material (FIG. 12). Included blasting material has a negative impact on the bone attachment on the implant.

FIGS. 7 to 10 show the superimposition of a coarse microstructure (structure size 20 μm to 80 μm) and a fine microstructure (structure size less than 1 μm) as a product of pretreatment method 1.

FIGS. 13 and 14 show the superimposition of a coarse microstructure from pretreatment method 1 and a fine microstructure from pretreatment method 2.

FIGS. 15 to 22 show the microstructures of four commercially available implants. The surfaces were etched or coated with titanium in a last process step. The respectively following figure shows a view in which a nanostructure should be visible. None of the four commercially available implant surfaces exhibits an appreciable nanostructure, which could have an influence on the wetting characteristics.

FIGS. 23 and 24 show a titanium surface which was etched according to pretreatment process 2. It can be seen in FIG. 22 that no appreciable nanostructure is present.

During manufacture, the titanium surfaces of FIGS. 29 to 37 were first subjected to pretreatment method two in order to produce the microstructure. The nanostructures were produced by means of pulsed electrolysis. After several weeks of exposure to the normal atmosphere, all three surface variants exhibited a wetting angle of less than 15°. As a result of the microstructuring, the surface "sucked" itself full of water upon contact therewith even weeks after manufacture and storage in normal atmosphere.

LIST OF REFERENCE SYMBOLS

2 Post part
4 Assembly part
6, 7, 8, 9 Step
10, 11, 12 Thread
14 Apical end
15 Coronal end
16 Borehole
18 Internal thread
20 Through hole
22 Crown
24 Implant base body
26 Holder
28, 30 Electrode
32 Wire
34 Holding element

The invention claimed is:

1. A process for producing a metal body with a surface having nanoscopic pores or a nanoscopic structure, comprising: applying an alternating current to a metal base body in an electrolysis bath, wherein the electrolysis bath is laced with ions selected from the group consisting of ions from groups V to VII of the periodic table and an element comprising the ions as a component, and wherein the amplitude of the alternating current applied to electrodes of the electrolysis bath is increased in successive time intervals in a step-by-step manner.

2. The process as set forth in claim 1, wherein the metal base body consists of titanium or of a titanium-containing alloy, particularly laced with chromium.

3. The process as set forth in claim 1, wherein a sulfuric acid ($H_2SO_4$) or one of the acids nitric acid ($HNO_3$), hydrochloric acid (HCl), nitrous acid ($HNO_2$), phosphoric acid ($H_3PO_4$), sulfurous acid ($H_2SO_3$), fluoric acid (HF), a mixture of these acids or an aqueous solution with salts of the named acids is used as an electrolysis bath.

4. The process as set forth in claim 1, wherein an aqueous sodium sulfate solution or an ammonium sulfate solution or a sodium nitrite solution or an ammonium nitrite solution is selected as electrolyte.

5. The process as set forth in claim 4, wherein an initial concentration of approximately 5 g sodium sulfate ($Na_2SO_4$) or ammonium sulfate (($NH_4$)$_2SO_4$) or sodium nitrite ($NaNO_2$) or ammonium nitrite ($NH_4NO_2$) per 30 ml water is set.

6. The process as set forth in claim 1, wherein a time interval of approximately 5 minutes or more is selected for each successive time interval.

7. The process as set forth in claim 1, wherein a working temperature of about 40° C. to 120° C., preferably of about 50° C., is set for the electrolyte.

8. The process as set forth in claim 1, wherein a dental implant is manufactured.

9. The process as set forth in claim 8, wherein an implant base body provided with a microstructured surface is used as a metal base body.

10. A process as set forth in claim 1, wherein, in order to structure the surface in the range of 0.25 μm to 500 μm, the ambient medium is or also contains chlorine, chlorine ions and/or a chlorine-containing acid, preferably hydrochloric acid, as a component.

11. A process as set forth in claim 1, wherein, in order to structure the surface in the range of 1 nm to 250 nm, the ambient medium also is or contains as a component sulfur, sulfur ions and/or a sulfur-containing acid, preferably sulfuric acid.

12. A process as set forth in claim 1, wherein, in order to structure the surface in the range of 0.25 μm to 100 μm, the ambient medium also is or contains as a component nitrogen, nitrogen ions and/or a nitrogen-containing acid, preferably nitric acid.

13. A process as set forth in claim 1 wherein, in order to structure the surface in the range of 1 nm to 250 nm, the ambient medium also is or contains as a component nitrogen, nitrogen ions and/or a nitrogen-containing acid, preferably nitric acid.

14. A process as set forth in claim 1, wherein, in order to structure the surface in the range of 1 nm to 250 nm, the ambient medium also is or contains as a component phosphorous, phosphorous ions and/or a phosphorous-containing acid, preferably phosphoric acid.

15. A process as set forth in claim 1, wherein, in order to structure the surface in the range of 1 nm to 250 nm, the ambient medium also is or contains as a component fluorine, fluorine ions and/or a fluorine-containing acid, preferably fluoric acid.

16. The process of claim 1, wherein the amplitude of the alternating current is increased in steps of approximately 5 V or less, from approximately 5 V to approximately 15 V.

17. A process for surface enlargement, comprising:
applying an alternating current to a metal body made of a metal selected from the group consisting of titanium, chromium, iron, zirconium, tantalum, niobium and of an alloy with at least one of these metals as the main component, in a liquid electrolyte which contains at least one ion selected from the group consisting of an element of group V to VII of the periodic table or comprising such an element as a component,
wherein the amplitude of the voltage is increased in successive time intervals in a step-by-step manner.

18. A process as set forth in claim 17, wherein the medium used in the process is a water-containing electrolyte which contains ions with at least one of the elements from the fifth, sixth or seventh main group.

19. A process as set forth in claim 17, wherein the medium used in the process contains at least one acid with an element from the fifth, sixth or seventh main group.

20. A process as set forth in claim 17, wherein the medium used in the process consists partially, preferably entirely of at least one melted salt or a chemical compound which consists of at least one of the elements from the fifth, sixth or seventh main group.

21. The process of claim 17, wherein the amplitude of the alternating current is increased in steps of approximately 5 V or less, from approximately 5 V to approximately 15 V.

* * * * *